United States Patent [19]

Bacon, Jr. et al.

[11] Patent Number: 5,283,199
[45] Date of Patent: Feb. 1, 1994

[54] CHLORINE DIOXIDE MONITOR BASED ON ION MOBILITY SPECTROMETRY WITH SELECTIVE DOPANT CHEMISTRY

[75] Inventors: Allan T. Bacon, Jr., Joppatowne; Richard C. Getz, Baltimore, both of Md.

[73] Assignee: Environmental Technologies Group, Inc., Baltimore, Md.

[21] Appl. No.: 778,783

[22] Filed: Oct. 18, 1991

Related U.S. Application Data

[63] Continuation-in-part of Ser. No. 746,464, Aug. 16, 1991, Pat. No. 5,234,838, which is a continuation-in-part of Ser. No. 687,594, Apr. 17, 1991, Pat. No. 5,095,206, which is a continuation-in-part of Ser. No. 534,701, Jun. 1, 1990, Pat. No. 5,032,721.

[51] Int. Cl.$^5$ .................. G01N 24/00; B01D 59/44
[52] U.S. Cl. .................. 436/173; 436/124; 422/82.01; 422/83; 422/98; 250/282; 250/286; 250/287; 250/288
[58] Field of Search .............. 436/124, 171, 173; 422/82.01, 82.02, 82.05, 83, 90, 98; 250/282, 286, 287, 288

[56] References Cited

U.S. PATENT DOCUMENTS

| | | | |
|---|---|---|---|
| 3,717,028 | 2/1973 | Annino et al. | 73/23.36 |
| 3,755,085 | 8/1973 | Tivin et al. | 435/263 |
| 4,374,090 | 2/1983 | McClure | 422/98 |
| 4,378,499 | 3/1983 | Spangler et al. | 250/288 X |
| 4,390,784 | 6/1983 | Browning et al. | 250/286 |
| 4,445,038 | 4/1984 | Spangler et al. | 250/287 |
| 4,551,624 | 11/1985 | Spangler et al. | 422/98 X |
| 4,712,008 | 12/1987 | Vora et al. | 250/287 |
| 4,777,363 | 10/1988 | Eiceman et al. | 250/287 |
| 4,797,554 | 1/1989 | Blanchard et al. | 250/282 |
| 4,839,143 | 6/1989 | Vora et al. | 250/281 |
| 4,950,893 | 8/1990 | Reategui et al. | 250/282 |
| 5,032,721 | 7/1991 | Bacon et al. | 250/282 |
| 5,095,206 | 3/1992 | Bacon, Jr. et al. | 250/286 X |

OTHER PUBLICATIONS

Bacon et al.; "Detection of HF Using Atmospheric Pressure Ionization (API) and Ion Mobility Spectrometry (IMS)"; Jun. 3, 1990.

*Primary Examiner*—Lyle A. Alexander
*Assistant Examiner*—Maureen M. Wallenhorst
*Attorney, Agent, or Firm*—Leonard Bloom

[57] ABSTRACT

An improved ion mobility spectrometer (IMS) and method for operating the same which enables analysis of chlorine dioxide in a mixture of gases which also includes the interferant chlorine. A controlled concentration of an amine such as methylamine is added to the air carrier gas stream prior to application of the carrier gas stream. The amine suppresses the chlorine peak, thereby improving the specificity of the IMS to chlorine dioxide. The IMS of the present invention also includes an improved membrane filter for pre-filtering chlorine, and a software algorithm for accommodating peak drift.

44 Claims, 3 Drawing Sheets

CHLORINE DIOXIDE MONITOR BASED ON ION MOBILITY SPECTROMETRY WITH SELECTIVE DOPANT CHEMISTRY

CROSS-REFERENCE TO RELATED APPLICATIONS

This application is a continuation-in-art of application Ser. No. 746,464, filed Aug. 16, 1991, (now U.S. Pat. No. 5,234,838) which is a continuation-in-part of application Ser. No. 687,594, filed Apr. 17, 1991, (now U.S. Pat. No. 5,095,206) which is a continuation-in-part of application Ser. No. 534,701, filed Jun. 1, 1990 (now U.S. Pat. No. 5,032,721).

1. Field of the Invention

The present invention relates to ion mobility spectrometry with improved specificity to certain gases, and more particularly, to the use of a dopant and related improvements which enhance the specificity of detection of chlorine dioxide.

2. Background of the Invention

There is a growing commercial demand for monitoring systems which are capable of identifying and quantifying constituent gases in a sample. In part, the demand arises from the need to prevent hazardous gases from escaping into the air. Governments worldwide are beginning to enact clean air regulations which limit the emissions of hazardous gases from processing plants and storage facilities. These regulations implicitly compel the use of a monitor to enable corrective action in case the concentration of hazardous gas exceeds a specified level, and to provide an early warning of impending danger to plant personnel and the public.

One notable gas which requires the use of a monitor is chlorine dioxide. Chlorine dioxide is a highly toxic and explosive substance widely used in many manufacturing and chemical bleaching processes, especially in the paper industry. The dangerous properties of chlorine dioxide have inspired "safe" limits of approximately 0.1 parts per million (ppm). Highly sensitive and reliable monitors are necessary to insure that these safe limits are complied with.

Conventional monitoring systems rely on wet chemical collection and analysis procedures which are inaccurate, time-consuming, labor intensive, and which fail to provide real-time results. For instance, sensors which employ electrochemical cells lack the sensitivity necessary to monitor trace amounts (0.1 ppm) of chlorine dioxide. This problem is compounded by the inevitable presence of chlorine gas along with the chlorine dioxide. Chlorine gas is commonly present along with chlorine dioxide, and the chlorine acts as a strong interferant in detecting chlorine dioxide.

Ideally, a chlorine dioxide monitor should be capable of accurately detecting and quantifying trace amounts of chlorine dioxide at concentrations well below 0.1 ppm. In addition, the monitor should operate continuously over extended periods of time without the need for frequent maintenance or calibration.

An Ion Mobility Spectrometer (IMS) is a well-known analytical tool capable of accurate and trouble-free analysis of the constituents in a sample. Basically, an IMS comprises an analyzer cell, means for ionizing samples of an analyte admitted to the cell and means for determining the times required for the ions of the various substances present in the cell to traverse a specific length of the cell under the influence of an electric field and against the force of a stream of drift gas flowing through the cell in a direction opposite to that of the electric field. A representative analyzer cell is disclosed in U.S. Pat. No. 4,390,784 issued to Browning, et al. A stream of purified gas may be used as a carrier gas to introduce the analyte sample into the cell, and a stream of purified gas may also be used as the drift gas. Generally, there is no maintenance required of an IMS other than the occasional replacement of filters and membranes for purifying the carrier and drift gases, radiation wipe tests, and calibration. An IMS would be well-suited for use in a monitoring system designed to detect and quantify chlorine dioxide.

Unfortunately, it has been found that an IMS operated in a conventional manner, using air as the carrier and drift gases, may lack the specificity necessary to detect chlorine dioxide under certain conditions. The conditions arise when certain interferants are present in the sample, most notably, chlorine. This is because the chlorine peak in an IMS disrupts the chlorine dioxide peak. Hence, it becomes very difficult to distinguish the amplitude of the ion current due to the chlorine dioxide gas from the ion current due to the chlorine gas.

In U.S. Pat. No. 5,032,721, an IMS monitor is disclosed which uses a dopant to improve the specificity for acid gases. The dopant is selected from the group of substituted phenols, and improves the ability of the gas monitor to detect the general presence of acid gases such as hydrogen fluoride, hydrogen chloride, chlorine, nitrogen dioxide, sulfur dioxide, carbonyl sulfide, and numerous others. However, the '721 patent does not solve the problem of interference from such gases.

In U.S. Pat. No. 5,095,206, an IMS monitor is disclosed with improved specificity to an acid gas in a mixture of acid gases. A controlled concentration of sulfur dioxide dopant is added to the air carrier gas stream prior to application of the carrier gas stream. In the IMS, the reactant ions formed by the $SO_2$ have a higher charge affinity than many potential interferants, but a lower charge affinity than the target compound. This allows detection of the ion peak due to the target compound without interference.

It would be greatly advantageous to incorporate the above-described teachings in an IMS specifically designed for the analysis of chlorine dioxide, where the ion current peak due to chlorine in the sample is suppressed to eliminate interference with the chlorine dioxide peak.

SUMMARY OF THE INVENTION

It is, therefore, an object of the present invention to provide a method of ion mobility spectrometry with improved specificity for detecting chlorine dioxide in a sample containing other constituents, whereby interference and false indications resulting from the other constituents are eliminated.

It is a specific object of the present invention to provide a method and apparatus based on ion mobility spectrometry which suppresses interference from chlorine in a sample containing both chlorine dioxide and chlorine, to thereby improve the specificity toward chlorine dioxide.

It is a broader object of the present invention to provide a method for eliminating chlorine interference in any type of instrumental analysis.

According to the present invention, the above-described and other objects are accomplished by providing an ion mobility spectrometer with improved specificity for detecting chlorine dioxide in the presence of interferants such as chlorine. The spectrometer generally includes an analyzer cell having an inlet region, a reaction region, an ionization source in said reaction region, means for introducing at least one dopant comprising an amine into the reaction region, a shutter grid, a drift region, an ion current detector for detecting ions transiting said cell drift region, and means for measuring the transit times through the cell drift region of ions generated in the cell reaction region and released into the drift region through the shutter grid. The method of operation for the above-described apparatus includes the steps of applying a drift gas stream of air to the cell drift region, mixing an amine with a carrier gas stream of air to create a doped carrier gas stream, introducing a test sample into the analyzer cell inlet region, applying the carrier gas stream to the cell inlet region to carry the test sample into the cell reaction region, and measuring an ion current at the ion current detector at a time corresponding to the transit time through the cell drift region of ions generated by the test sample in the cell reaction region. The amine reacts with chlorine in the sample to suppress the ion peak due to chlorine, thereby eliminating interference with the chlorine dioxide peak. Consequently, the amine dopant improves the selectivity of the ion mobility spectrometer.

In accordance with a broader aspect of the present invention, a method is taught for eliminating interference from chlorine in any instrumental analysis of chlorine dioxide. The method comprises the steps of mixing an amine with a test sample of gas to create a doped test sample, ionizing said test sample, and analyzing constituents in said test sample based on a charge affinity of ions generated therefrom, whereby said amine reacts with chlorine in said test sample to form a compound having a charge affinity which differs from chlorine.

BRIEF DESCRIPTION OF THE DRAWINGS

Other objects, features and advantages of the present invention will become more apparent from the following detailed description of preferred embodiments and certain modifications thereof when taken together with the accompanying drawings, in which.

DETAILED DESCRIPTION OF THE PREFERRED EMBODIMENT(S)

Figure 1:
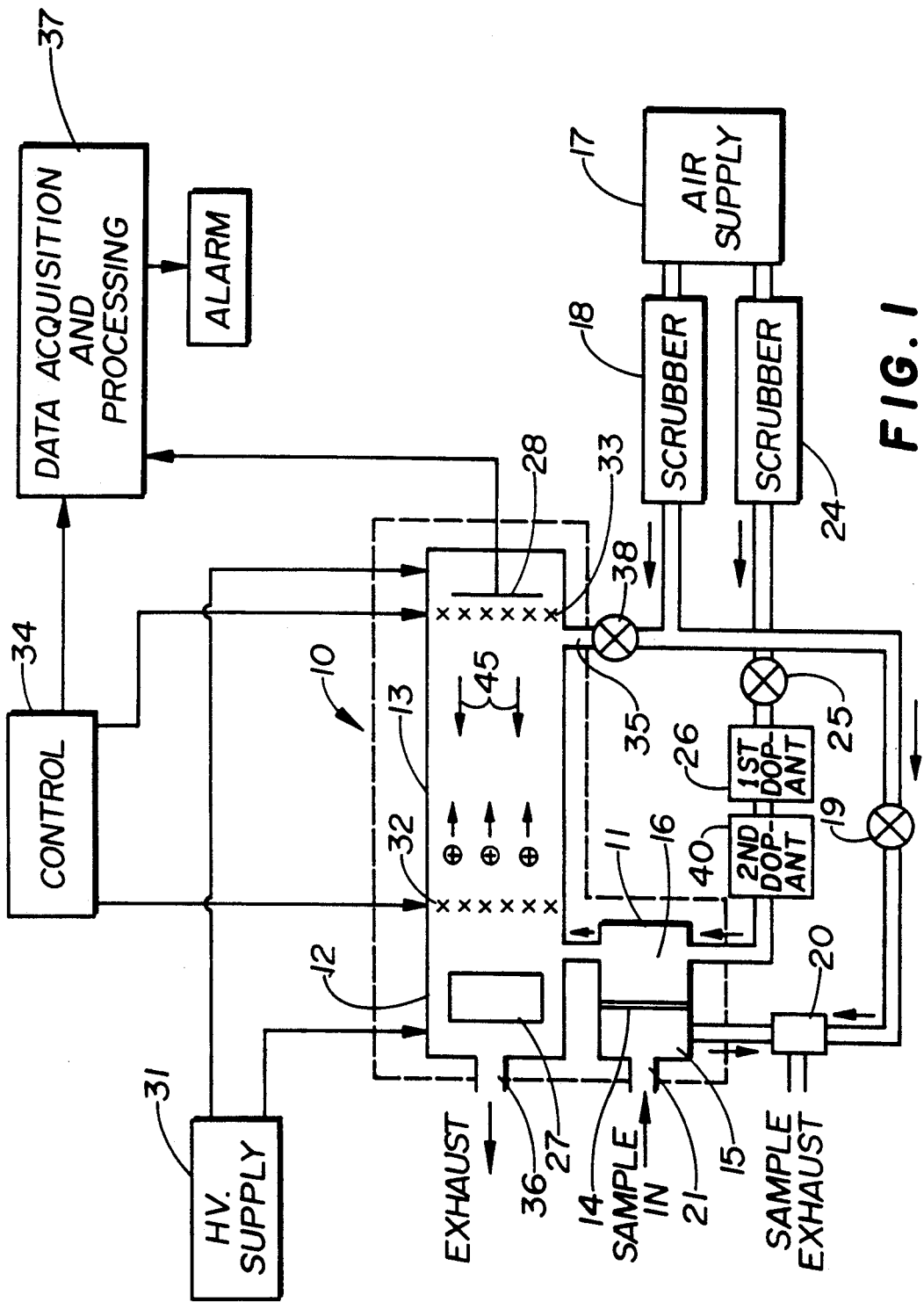
FIG. 1 is a functional block diagram of an Ion Mobility Spectrometer according to the present invention.

Referring to FIG. 1, the preferred apparatus of the present invention comprises an IMS analyzer cell 10 similar to that disclosed in U.S. Pat. No. 4,390,784 issued to Browning, et al., with certain improvements to be described.

Cell 10 is divided into an inlet region 11, a reaction region 12 and a drift region 13. Inlet region 11 is partitioned by a permeable membrane 14 into a sample chamber 15 and an inlet chamber 16. Air from a regulated pressure air supply 17 is passed through a scrubber 18, flow regulator 19 and venturi 20 to an exhaust. The air flow through venturi 20 inducts a sample of gas into sample chamber 15 and through membrane 14.

In the preferred embodiment, membrane 14 comprises a 0.001 inch-thick diaphragm of silicon/polycarbonate. Although many types of filters may be used instead, it has been found that silicon/polycarbonate is best able to remove $Cl_2$ without removing $ClO_2$ in the process. Hence, membrane 14 partially eliminates $Cl_2$ interference without removing $ClO_2$ from the sample.

The sample is inducted through membrane 14 and into inlet chamber 16. The temperature of sample chamber 15 and inlet chamber 16 is preferably maintained by a thermostat to insure a constant concentration of sample constituents.

The constituents passing through membrane 14 into chamber 16 are then swept from chamber 16 by a carrier gas into the reaction region 12 of analyzer cell 10.

In the preferred embodiment, the carrier gas stream comprises air from air supply 17 that is passed through a scrubber 24 primarily to remove water vapor therefrom, and through flow regulator 25. Alternatively, nitrogen and many other inert gases may be used in place of air provided that the dew point is below $-40°$ F. and some oxygen is present. This constraint is useful when sampling flammable mixtures.

After passing through scrubber 24 and flow regulator 25, the carrier gas stream is flowed around a first permeation tube 26, where a controlled concentration of a first dopant is added to the air stream. The first permeation tube 26 may be temperature-controlled, the temperature preferably being maintained by a thermostat to insure a constant flow of the first dopant. In accordance with the teachings of U.S. Pat. No. 5,032,721, the first dopant comprises a substituted phenol compound, with methyl salicylate (MS) or 2-hydroxyacetophenone (2-HAP) being preferred. The drift times of the ions generated from the carrier gas when doped with MS differ from the drift times of the ions generated from the chlorine dioxide, enabling better identification and quantification of the chlorine dioxide in the sample. The disclosure of the '721 patent is incorporated herein by reference to explain the operation of the first dopant in more detail.

Before it reaches the inlet region 11, the carrier gas stream is flowed around a second temperature-controlled permeation tube 40, where a controlled concentration of a second dopant is added to the air stream. Once again, the temperature of the second permeation tube is preferably maintained by a thermostat to insure a constant flow of dopant.

It is essential to the present invention that the second dopant react with chlorine to form a compound having a different charge affinity. The resulting difference between the chlorine dioxide and chlorine ions will improve the specificity of the IMS because the ion current peak attributable to the chlorine will no longer interfere with the peak due to the chlorine dioxide. Several compounds from among the class of compounds known as amines will react with chlorine in the desired manner, and hence may be used in the present invention. Methylamine completely suppresses the chlorine peak. Therefore, methylamine is used in the preferred embodiment of the invention. However, other amines may be equally effective, and ammonia or nitrogen-containing compounds which exhibit properties similar to the amines may be used as well.

Reaction region 12 contains an ionization source 27 which generates product ions from the constituents swept into region 12 by the carrier gas. Source 27 may be of the β-particle ionizing radiation type which is usually formed of a ring of Ni63. Alternatively, source 27 may be one of a variety of sources known in the field, such as ultraviolet, corona discharge, thermionic, etc.

The product ions formed in region 12 are driven in the direction of an ion detector 28, located at the end of drift region 13 opposite reaction region 12, by an electrostatic field generated along regions 12 and 13 by a high voltage supply 31. Reaction region 12 is partitioned from drift region 13 by a shutter grid 32, and ion detector 28 is separated from drift region 13 by an aperture grid 33. Shutter grid 32 and aperture grid 33 are separately biased by voltages from a control circuit 34. The drift gas, admitted to drift region 13 through port 35, flows continuously through drift region 13 and reaction region 12, exhausting therefrom through exhaust vent 36.

Preferably, the drift gas likewise comprises air from air supply 17 which is passed through scrubber 18 and flow regulator 38 into port 35. As with the carrier gas, nitrogen or several other inert gases may be used in place of air provided that the gas has a dew point below −40° F. and contains some oxygen. Like the carrier gas, the drift gas stream may also be passed through a temperature-controlled permeation tube (not shown) for the purpose of introducing a controlled concentration of dopant to the air stream.

The ion mobility spectrometer of the present invention may be operated in either the positive mode to generate positive product ions at the source 27, or the negative mode to generate negative ions at the source 27.

If operation is in the positive mode, shutter grid 32 is biased positively for the major part of a scan cycle to block the product ions in reaction region 12 from entering drift region 13. At the beginning of a scan period, the bias is changed briefly to allow a cloud of ions to enter drift region 13. The ions accelerate along the length of drift region 13 toward the detector 28 under the influence of the electric field and against the force of the counter-flowing drift gas (represented by the arrows 45). The product ions created by the various constituents traverse the drift region in different time periods, depending upon the charge/molecular size characteristics of each constituent. If a complete spectrum is to be taken, aperture grid 33 may be neutrally biased so that the arrival times of each of the various ion groups at detector 28 may be measured. If the IMS is intended to be responsive to only a single specific substance, the aperture grid may be biased so as to repel all ions except for those arriving at a time corresponding to the predetermined characteristic arrival time of ions for the substance of interest.

Alternatively, the IMS may be operated in the enhancement mode, as disclosed and claimed in U.S. Pat. No. 4,950,893, issued Aug. 21, 1990 to J. A. Reategui, et al., for "Method and Apparatus for Enhanced Ion Spectrum Generation and Detection in Ion Mobility Spectrometry", assigned to the assignee of the present application. Briefly, in the enhancement mode, the shutter grid 32 of the IMS is biased open for the major portion of a scan cycle allowing ions to enter drift region 13 continuously upon their generation in the cell reaction region 12. At the beginning of a scan cycle, the shutter grid 32 is momentarily biased closed, thereby creating a void in the otherwise continuous stream of ions transiting from reaction region 12 into drift region 13. The void traverses drift region 13 and becomes separated into secondary voids which arrive at ion detector 28 at different transit times, in much the same manner as the ion groups which traverse and become separated in the conventional mode. The substantially steady stream of ions that enters drift region 13 during the open period of the shutter grid establishes a baseline ion current at detector 28. The arrival of a secondary void at detector 28 creates a negative peak in the base line current. The arrival time at detector 28 of a negative peak characterizes the identity of one constituent substance of the test sample, and the amplitude of the negative peak characterizes the concentration of the constituent substance in the test sample. Operation of an IMS in the enhancement mode has the advantages of producing better resolution of the separated ion current peaks and of providing a means permitting continuous calibration of the IMS.

Figure 2:
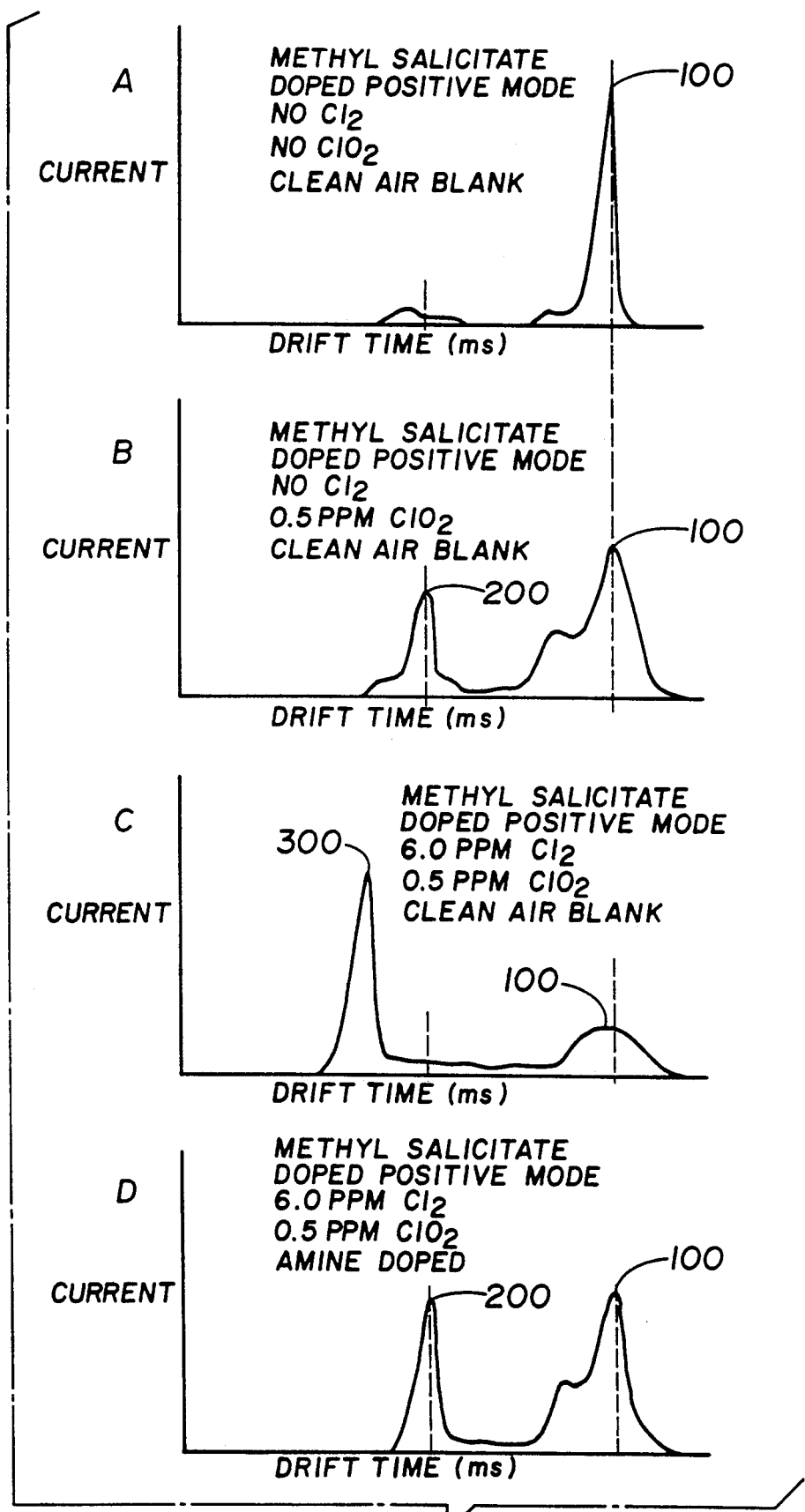
FIG. 2 is a comparative spectrograph showing the ion current peaks produced in the IMS of FIG. 1 by a test sample in which trace amount of chlorine and/or chlorine dioxide are/are not present. The graphs illustrate the effects of methylamine dopant on IMS specificity toward chlorine dioxide.

FIG. 2 is a comparative spectrograph showing the ion current peak produced when purified air doped with methyl salicylate is used as the carrier gas, and the IMS is operated in the negative mode. In graph A, no chlorine dioxide or chlorine is present in the test sample. The ion current peak 100 attributable to the methyl salicylate appears at an arrival time of approximately 16 milliseconds (ms). Graph B of FIG. 2 shows the ion current peak produced when purified air doped with methyl salicylate is used as the carrier gas, and 0.5 ppm of chlorine dioxide is present in the sample. Again, the IMS is operated in the negative mode. The peak 200 in graph B due to the chlorine dioxide occurs at approximately 11 milliseconds (ms). The two peaks 100 and 200 are distinguishable by the IMS under these conditions, and an accurate quantitative measurement could be made. As disclosed in U.S. Pat. No. 5,032,721, the methyl salicylate dopant is responsible for changing the drift times of the ions generated from the carrier gas. Hence, the peak 100 due the doped carrier gas is separated from the peak 200 generated from the chlorine dioxide, enabling better identification and quantification of the chlorine dioxide in the sample.

The conditions of FIG. 2B appear only in the laboratory. In most applications, there would inevitably be significant amounts of chlorine gas in the sample as well. The chlorine ($Cl_2$) acts as an interferant.

FIG. 2C demonstrates the complete impracticality of distinguishing chlorine dioxide in a sample containing chlorine when all other conditions are the same as in FIGS. 2A and B. In graph C, 0.5 ppm of chlorine dioxide is present in the test sample along with 6.0 ppm of chlorine. The ion current peak due to the chlorine dioxide (peak 200 in FIG. 2b) is completely suppressed along with the ion current peak that is attributable to the "$O_2(H_2O)_x^-$ (peak 150 in FIG. 2b). The chlorine peak 300 steals charge from the ion current peak produced by the chlorine dioxide as well as other peaks that may be present. The resulting specificity is decreased to the point where the chlorine dioxide peak cannot be detected. Thus, it becomes impossible to quantify the amount of chlorine dioxide in the sample.

The amine dopant administered by permeation tube 40 in accordance with the present invention reacts with the chlorine, and the resulting compound produces ions with a different charge affinity than ions produced by chlorine. This results in the ion current peak 300 of FIG. 2C being completely suppressed by the amine dopant, as shown in FIG. 2D. The peak 200 owing to the chlorine dioxide becomes plainly distinguishable.

The conditions under which the results of FIG. 2 were obtained were as follows:
carrier gas flow—50 cc/min;
drift gas flow—100 cc/min;
carrier and drift gas—air;
inlet sample flow rate—200 cc/min.
inlet region temperature—50°;
cell temperature—50°;
operation—negative ion mode;
shutter grid pulse width—200 us;
inlet membrane—0.001 inch silicon/polycarbonate.
permeation rate of methyl salicylate—approx. 30 ug/min.
permeation rate of methylamine—approx. 2 ug/min.

It should be noted that none of the above parameters are limiting, and that the invention can be practiced with wide deviations therefrom. For instance, it is not necessary to introduce methyl salicylate dopant into the carrier gas. Moreover, the method of eliminating interference from chlorine is equally applicable in any ionization analysis of a sample containing both chlorine dioxide and chlorine.

A further feature of the preferred embodiment of the present invention is a means for compensating for extraneous variations in the IMS peak current measurements. Environmental changes and other extraneous variables may cause changes in any of the peaks to be measured by the IMS. Ambient atmospheric pressure changes cause the peaks to shift in terms of drift time position. Since the $ClO_2$ peak is proximate the peak normally produced by air, the extraneous shifts may cause false positive indications of chlorine dioxide. Other extraneous variables can cause changes in the peak height. Hence, a consistently accurate determination of the chlorine dioxide concentration cannot be calculated directly from the measured peak height of chlorine dioxide. Instead, a peak height ratio $R_c$ of chlorine dioxide ion current over the reactant ion current can be used. Since the measured peak heights are all subject to the same extraneous effects, the resulting changes in peak height are canceled in the ratio $R_c$. Any resulting drift in peak location is accounted for by recalculating an expected peak location for the second peak (which is attributable to chlorine in the sample), and for the target peak (which is attributable to $O_2(H_2O)_x^-$ dioxide in the sample) each time the peak attributable to the carrier gas doped with methyl salicylate is measured. The data is smoothed by averaging each calculated ratio $R_c$ with the prior 29 calculated $R_c$ ratios.

The above-described compensation is carried out by a software program stored on the internal processor of a conventional IMS. Generally, the IMS processor is programmed to look within a window of potential drift times in which the expected ion peaks will occur. The processor determines the highest point within the window, the highest point being attributable to the methyl salicylate reactant ion peak 100. The drift time corresponding to the highest point is then determined and is multiplied by a first ratio stored in memory to estimate the location of the $O_2(H_2O)_x$ peak 150. The drift time corresponding to the highest point is also multiplied by a second ratio stored in memory to estimate the location of the $ClO_2$ peak 200. The IMS measures the ion current at both of the estimated peak locations and calculates a third ratio using the measured values, the third ratio being equal to the $ClO_2$ ion current peak 200 divided by the sum of the methyl salicylate ion current peak 100 plus the $O_2(H_2O)_x$ peak 150. The calculated third ratio is compared to a look-up table stored in memory to determine the concentration of chlorine dioxide.

Figure 3:
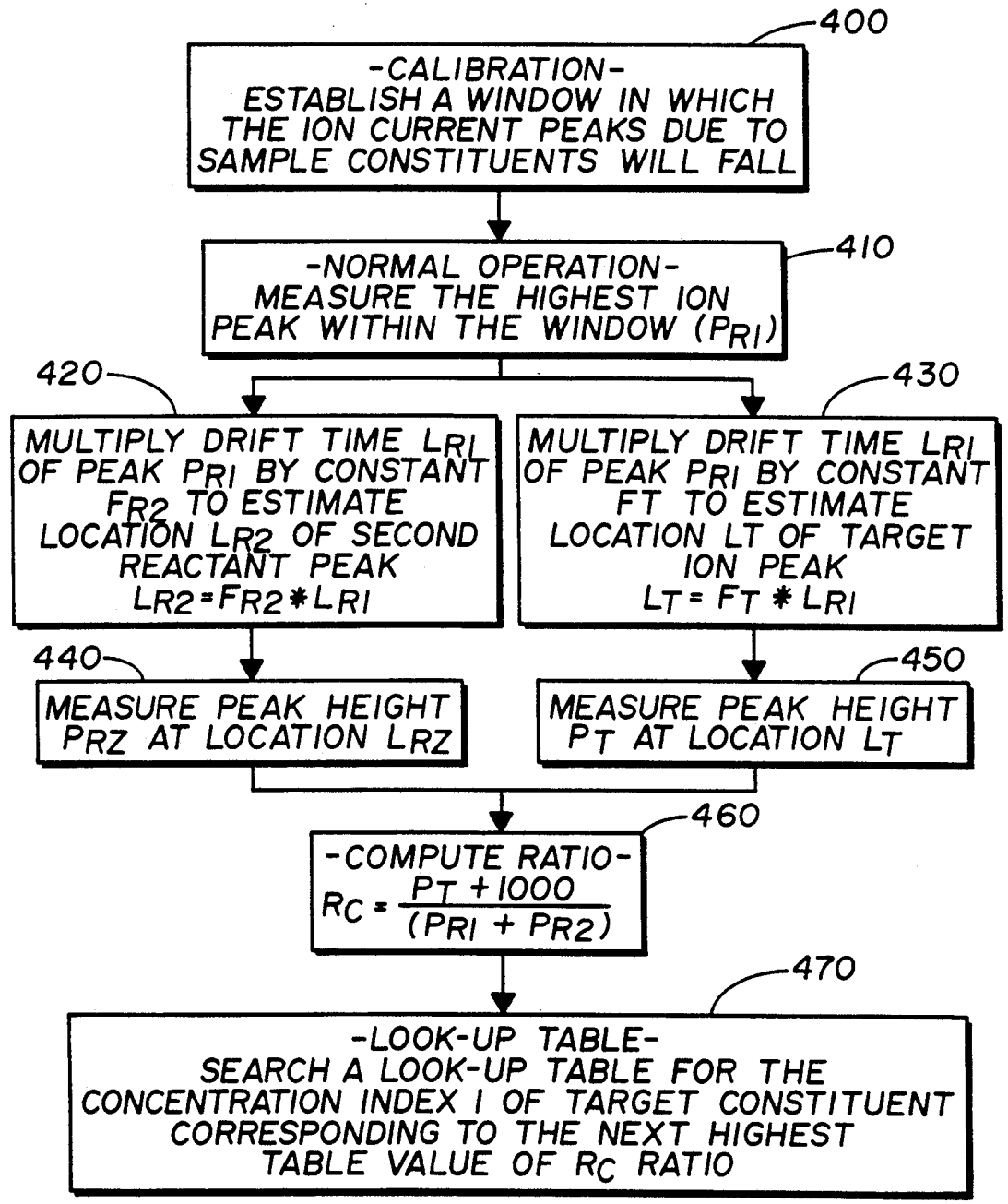
FIG. 3 illustrates a flow chart which is a preferred embodiment of a program which compensates for extraneous variations in the IMS peak current measurements.

FIG. 3 illustrates a detailed flow chart of the above-described program.

The first step 400 is accomplished during zero concentration calibration of the IMS. A drift time window L is established in which the expected ion peaks due to the reactant ion constituents will occur.

As the IMS is operated in step 410, the highest ion peak $P_{R1}$ within window L is measured. Peak $P_{R1}$ is attributable to the carrier gas doped with methyl salicylate.

In step 420, the drift time $L_{R1}$ of peak $P_{R1}$ is multiplied by a predetermined constant $F_{R2}$ to estimate the drift time $L_{R2}$ of the second peak, which peak is attributable to $O_2(H_2O)_x^-$ in the sample.

In step 440, the IMS is used to measure the actual peak height $P_{R2}$ occurring at the estimated drift time $L_{R2}$.

In step 430, the drift time $L_{R1}$ of peak $P_{R1}$ is multiplied by a predetermined constant $F_{RT}$ to estimate the drift time $L_T$ of the target peak, which peak is attributable to chlorine dioxide in the sample.

In step 450, the IMS is used to measure the actual peak height $P_T$ occurring at the estimated drift time $L_T$.

In step 460, the ratio $R_C$ is computed based on the actual peak height $P_{R2}$, the actual peak height $P_T$, and the ion peak $P_{R1}$. The process should be repeated at least thirty times to obtain an equal number of values of ratio $R_c$. An average ratio $R_A$ is then determined from the values of $R_c$.

In step 470, the ratio $R_A$ is compared to a look-up table of corresponding concentration indices. The concentration index i which corresponds to the next highest value for ratio $R_A$ in the look-up table is determined.

Since the concentration index i represents the concentration of the target constituent in the sample in 0.01 ppm increments, the total concentration C can be determined by multiplying i by 0.01.

Having now fully set forth the preferred embodiment and certain modifications of the concept underlying the present invention, various other embodiments as well as certain variations and modifications of the embodiments herein described will obviously occur to those skilled in the art upon becoming familiar with said underlying concept. It is to be understood, therefore, that within the scope of the appended claims, the invention may be practiced otherwise than as specifically set forth herein.

We claim:

1. A method for eliminating interference from chlorine when analyzing a test sample, the method comprising the steps of:
   admitting a test sample of gas to an ion mobility spectrometer;
   mixing an amine dopant with said test sample, whereupon said dopant reacts with chlorine in said test sample to form a compound having a charge affinity different from that of chlorine; and
   analyzing a constituent other than chlorine in said test sample substantially free of interference from chlorine in said test sample.

2. The method of claim 1, wherein said amine dopant comprises methylamine.

3. The method of claim 1, wherein said step of mixing said amine dopant comprises mixing said amine dopant at a concentration greater than a concentration of said chlorine in said test sample.

4. The method of claim 3, wherein said step of mixing amine dopant is accomplished by mixing a gas stream with said test sample, flowing said gas stream and test sample over a permeation tube and permeating said amine dopant through said permeation tube.

5. The method of claim 4, wherein said gas stream comprises a carrier gas stream.

6. The method of claim 1, wherein said step of analyzing said constituent other than chlorine comprises analyzing said constituent using ion mobility spectrometry.

7. The method of claim 1, further comprising the step of prefiltering said test sample after admission thereof into said ion mobility spectrometer using a membrane filter to exclude chlorine from entering a carrier stream of gas.

8. The method of claim 1 wherein said step of admitting a test sample of gas into an ion mobility spectrometer further comprises continuous-flow introduction of said test sample.

9. A method for monitoring chlorine dioxide in a test sample, the method comprising the steps of:
   admitting a test sample of gas into an ion mobility spectrometer for monitoring of chlorine dioxide in said test sample;
   mixing an amine dopant with said test sample, whereupon said dopant reacts with chlorine when present in said test sample to form a compound;
   ionizing said test sample, whereby ions from said compound have a charge affinity which differs from a charge affinity of ions from chlorine dioxide in said test sample; and
   analyzing chlorine dioxide in said test sample substantially free of interference from chlorine.

10. The method of claim 9, wherein said amine dopant comprises methylamine.

11. The method of claim 9, wherein said step of mixing said amine dopant with said test sample further comprises mixing said amine dopant with a gas stream and applying said gas stream to carry said test sample to an ionization source, said amine dopant thereby mixing with said test sample.

12. The method of claim 11, wherein said step of mixing said amine dopant in said gas stream comprises mixing said amine dopant at a concentration greater than a concentration of chlorine in said test sample.

13. The method of claim 12, wherein said step of admitting a test sample of gas into an ion mobility spectrometer further comprises pre-filtering said test sample using a membrane filter to assist in removing chlorine.

14. The method of claim 13, wherein said membrane filter is a silicone polycarbonate composition filter.

15. The method of claim 11, wherein said step of mixing amine dopant with said gas stream is accomplished by flowing said gas stream over a permeation tube containing said amine dopant, whereby said gas stream mixes with amine dopant permeating through said permeation tube.

16. The method of claim 15, wherein said permeation tube is maintained at a constant temperature to preserve a uniform concentration of dopant.

17. The method of claim 9 wherein said step of admitting a test sample of gas into an ion mobility spectrometer further comprises continuous-flow introduction of said test sample.

18. A method for operating an ion mobility spectrometer to monitor chlorine dioxide in a test sample, the method comprising the step of:
   introducing a test sample of gas into said ion mobility spectrometer for monitoring of chlorine dioxide in said test sample;
   mixing an amine dopant with said test sample, whereupon said dopant reacts with chlorine when present in said test sample to form a compound having a charge affinity different from that of chlorine;
   applying said doped test sample to an ionization source;
   generating an ion current by ionization of said test sample at said ionization source; and
   measuring said ion current at a distance from said ionization source;
   whereby a peak ion current is generated by said chlorine dioxide without interference from said chlorine.

19. The method according to claim 18, whereby said step of mixing an amine dopant with said test sample suppresses ion current generated by chlorine in said test sample, thereby attributing said measured ion current to chlorine dioxide in said test sample.

20. The method of claim 18, wherein said amine dopant comprises methylamine.

21. The method of claim 18, wherein said step of mixing said amine dopant with said test sample further comprises mixing said amine dopant with a carrier gas stream and applying said carrier gas stream to carry said test sample to said ionization source, said amine dopant thereby mixing with said test sample.

22. The method of claim 21, wherein said step of mixing said amine dopant in said carrier gas stream comprises permeating said amine dopant into said carrier gas stream at a permeation rate of approximately 2 micrograms per minute.

23. The method of claim 21, wherein said step of mixing amine dopant with said carrier gas stream is accomplished by flowing said carrier gas stream over a permeation tube containing said amine dopant, whereby said carrier gas mixes with amine dopant permeating through said tube.

24. The method of claim 23, wherein said permeation tube is maintained at a constant temperature to preserve a constant permeation rate of dopant.

25. The method of claim 18, wherein said step of mixing said amine dopant with said test sample further comprises mixing said amine dopant with a drift gas stream of air and applying said drift gas stream to said test sample at said ionization source, said amine dopant thereby mixing with said test sample.

26. The method of claim 25, wherein said step of mixing said amine dopant in said drift gas stream comprises permeating said amine dopant into said drift gas stream at a permeation rate of approximately 2 micrograms per minute.

27. The method of claim 25, wherein said step of mixing amine dopant with said drift gas stream of air is accomplished by flowing said drift gas stream over a permeation tube containing said amine dopant, whereby said drift gas mixes with amine dopant permeating through said tube.

28. The method of claim 27, wherein said permeation tube is maintained at a constant temperature to preserve a constant permeation rate of amine dopant.

29. The method of claim 18, wherein said ion mobility spectrometer is operated in a negative ion mode.

30. The method of claim 18, further comprising a step of pre-filtering said test sample to further assist in removing chlorine after introducing said test sample of gas into said ion mobility spectrometer.

31. The method of claim 30, wherein said step of pre-filtering said test sample comprises pre-filtering chlorine by use of a silicone polycarbonate composition filter.

32. The method of claim 18, further comprising mixing methyl salicylate with said test sample.

33. The method of claim 32, wherein said methyl salicylate is mixed with said test sample prior to introduction of said amine dopant.

34. The method of claim 33, wherein said step of mixing said methyl salicylate with said test sample further comprises mixing said methyl salicylate with a carrier gas stream and applying said carrier gas stream to carry said test sample to said ionization source, said methyl salicylate thereby mixing with said test sample.

35. The method of claim 34, wherein said step of mixing methyl salicylate with said carrier gas stream comprises permeating methyl salicylate into said carrier gas stream at a permeation rate of approximately 30 micrograms per minute.

36. The method of claim 34, wherein said step of mixing methyl salicylate with said carrier gas stream is accomplished by flowing said carrier gas stream over a permeation tube containing said methyl salicylate, whereby said carrier gas mixes with methyl salicylate permeating through said tube.

37. The method of claim 36, wherein said permeation tube is maintained at a constant temperature to preserve a constant permeation rate of methyl salicylate.

38. The method of claim 32, wherein said monitoring of chlorine dioxide in said test sample further comprises:
    establishing a window of drift times in which expected ion peaks will occur,
    measuring a first ion current of a highest ion peak within said window, said highest ion peak being attributable to said methyl salicylate,
    determining a first drift time of said highest ion peak,
    multiplying said first drift time by a predetermined first constant to determine an estimated drift time of ions from $O_2(H_2O)_x$,
    measuring a second ion current at said estimated drift time of $O_2(H_2O)_x$,
    multiplying said first drift time by a predetermined second constant to determine an estimated drift time of chlorine dioxide ions,
    measuring a third ion current at said estimated drift time of chlorine dioxide ions,
    determining a concentration ratio of said third ion current by dividing said third ion current by a sum of said first ion current and said second ion current.

39. The method of claim 38, further comprising the step of comparing said concentration ratio to a look-up table of concentration values to determine a concentration value for chlorine dioxide in said sample.

40. The method of claim 38, further comprising the step of determining at least 30 concentration ratios.

41. The method of claim 40, further comprising the steps of determining an average concentration ratio from said at least 30 concentration ratios, and comparing said average concentration ratio to a look-up table of concentration values to determine a concentration value for chlorine dioxide in said test sample.

42. The method of claim 41, wherein said concentration value in said comparison step is an incremental concentration value expressed in increments of 0.01 ppm.

43. The method of claim 42, further comprising the step of multiplying said incremental concentration value by 0.01 to determine a total concentration of chlorine dioxide in said test sample.

44. The method of claim 18 wherein said step of introducing a test sample of gas into said ion mobility spectrometer further comprises continuous-flow introduction of said test sample.

* * * * *

UNITED STATES PATENT AND TRADEMARK OFFICE
CERTIFICATE OF CORRECTION

PATENT NO. : 5,283,199
DATED : February 1, 1994
INVENTOR(S) : Bacon, Jr. et al.

It is certified that error appears in the above-indentified patent and that said Letters Patent is hereby corrected as shown below:

In column 6, line 54 " $\dot{O}_2(H_2O)_x^-$ " should read -- $O_2(H_2O)_x^-$ --.

In column 7, line 60 and 68, " $O_2(H_2O)_x$ " should read -- $O_2(H_2O)_x^-$ --.

In the Drawings:
In Figure 2, graphs A-D, "Positive" should read -- Negative --.

In Figure 2, graphs B and C, delete "Clean air blank".

Signed and Sealed this

Second Day of August, 1994

*Attest:*

BRUCE LEHMAN

*Attesting Officer*     *Commissioner of Patents and Trademarks*